(12) United States Patent
Längle et al.

(10) Patent No.: US 12,569,267 B2
(45) Date of Patent: Mar. 10, 2026

(54) SURGICAL INSTRUMENT AND ACTUATION DEVICE THEREFOR

(71) Applicant: KARL STORZ SE & CO. KG, Tuttlingen (DE)

(72) Inventors: Dominik Längle, Mülheim (DE); Janosz Schneider, Donaueschingen (DE); Jochen Stefan, Wald (DE); Sven Axel Grüner, Trossingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 94 days.

(21) Appl. No.: 18/291,052

(22) PCT Filed: Jul. 25, 2022

(86) PCT No.: PCT/EP2022/070823
§ 371 (c)(1),
(2) Date: Jan. 22, 2024

(87) PCT Pub. No.: WO2023/006678
PCT Pub. Date: Feb. 2, 2023

(65) Prior Publication Data
US 2024/0325040 A1 Oct. 3, 2024

(30) Foreign Application Priority Data

Jul. 28, 2021 (DE) .................... 10 2021 119 534.9

(51) Int. Cl.
*A61B 17/29* (2006.01)
*A61B 34/00* (2016.01)

(52) U.S. Cl.
CPC .............. *A61B 17/29* (2013.01); *A61B 34/71* (2016.02); *A61B 2017/2903* (2013.01); *A61B 2017/2936* (2013.01); *A61B 2034/715* (2016.02)

(58) Field of Classification Search
CPC ......... A61B 17/29; A61B 34/71; A61B 34/30; A61B 34/70; A61B 2017/2903;
(Continued)

(56) References Cited

U.S. PATENT DOCUMENTS

| | | | |
|---|---|---|---|
| 7,306,597 B2 | 12/2007 | Manzo | |
| 10,105,128 B2 | 10/2018 | Cooper et al. | |
| 2006/0048787 A1* | 3/2006 | Manzo | A61B 34/30 606/1 |

FOREIGN PATENT DOCUMENTS

| | | |
|---|---|---|
| DE | 102019121092 A1 | 2/2021 |
| JP | H0652601 A | 2/1994 |

(Continued)

OTHER PUBLICATIONS

International Search Report, Application No. PCT/EP2022/070823, mailed Nov. 15, 2022. ISA/European Patent Office.
(Continued)

*Primary Examiner* — Brooke Labranche
(74) *Attorney, Agent, or Firm* — Honigman LLP

(57) ABSTRACT

A surgical instrument includes an actuation device. The surgical instrument includes a hollow shaft having a tool at the distal end of the shaft. The tool includes two jaw parts, and the actuation device is operatively connected to an actuation rod mounted in the shaft so as to and move and close the jaw parts. The actuation device includes a cam wheel that is operatively connected to the actuation rod by a connection portion. The actuation device includes a bearing device that provides forced guidance of a cam-follower pin along a longitudinal axis, such that, when the cam wheel is rotated about a rotational axis of the cam wheel, a linear movement of the cam-follower pin, guided in the cam track, and the actuation rod operatively connected thereto is provided along the longitudinal axis.

10 Claims, 5 Drawing Sheets

(58) Field of Classification Search
CPC ...... A61B 2017/2936; A61B 2034/715; A61B
18/1442
See application file for complete search history.

(56) References Cited

FOREIGN PATENT DOCUMENTS

| | | | |
|---|---|---|---|
| WO | 2014/004242 | A1 | 1/2014 |
| WO | 2015088647 | A1 | 6/2015 |

OTHER PUBLICATIONS

International Preliminary Report on Patentability, Application No.
PCT/EP2022/070823, dated Jan. 18, 2024.

* cited by examiner

SURGICAL INSTRUMENT AND ACTUATION DEVICE THEREFOR

CROSS-REFERENCE TO RELATED APPLICATIONS

This application is the U.S. national stage of PCT/EP2022/070823 filed on Jul. 25, 2022, which claims priority of German Patent Application 10 2021 119 534.9 filed on Jul. 28, 2021, the contents of which are incorporated herein.

TECHNICAL FIELD

The disclosure relates to a surgical instrument and an actuation device therefor, for opening and closing jaw parts of a tool at the tip of the surgical instrument.

BACKGROUND

From the prior art, surgical instruments are known which can be guided manually or by a robot and which have a hollow shaft, at the distal end of which the tool tip with the tool is located, while a handle or an actuation unit is arranged at the proximal end of the shaft. The tool at the tool tip can be a gripping or cutting tool having at least two gripping or cutting elements (combined as jaw parts), wherein, for the purpose of opening and closing the jaw parts, the surgical instrument has an actuation mechanism which usually comprises an actuation element which is mounted axially in the shaft and, at the proximal end, is operatively connected to the actuation unit.

A surgical system disclosed in U.S. Pat. No. 10,105,128 B2 describes an actuation mechanism for opening and closing such jaw parts. For this purpose, cable rollers are used, with pull cables forming the actuation elements. This actuation mechanism requires an opening member and a closing member at the tool tip, to each of which a pull cable is attached. The opening and closing of the jaw parts is then performed by retracting the opening member or closing member relative to the other member in the direction of the shaft, using the associated pull cable.

Other actuation mechanisms use, as actuation element, a pull/push rod, which is more stable than pull cables, can transmit both pulling and pushing movements and is easier to install. In addition, a pull/push rod can also be used to transmit a rotational movement.

WO 2014/004242 A1 describes a surgical instrument having an axially movable pull rod for opening and closing the jaw parts of the tool at the tool tip. The actuation mechanism for the pull rod has a movable drive yoke which is operatively connected at one side to the proximal end of the pull rod and at the other side to a drive coil, in such a way that an actuation of the coil leads to a movement of the support yoke and thus to an axial displacement of the pull rod.

SUMMARY

Proceeding from this prior art, it is an object of the present disclosure to provide an improved actuation mechanism for opening and closing jaw parts of a tool at the distal tool tip of a surgical instrument.

This object is achieved by an actuation device having the features of claim 1.

The further object of providing a surgical instrument with an improved actuation mechanism is achieved by the surgical instrument having the features of independent claim 9.

Further developments/preferred embodiments are described in the dependent claims.

According to a first embodiment of the actuation device according to the disclosure, which is provided and designed for a surgical instrument having a hollow shaft with a tool at the distal end of the shaft, wherein the tool has at least two jaw parts, the actuation device is arranged at the proximal end of the shaft. It is operatively connected to an actuation rod which, for the purpose of opening and closing the jaw parts, is mounted in the shaft in a manner axially movable in the direction of a longitudinal axis of the shaft. According to the disclosure, it is provided that the actuation device has a cam wheel with a cam track and a cam-follower pin. The cam-follower pin has a driver section and a connection section, wherein the cam-follower pin, which extends parallel to the axis of rotation of the cam wheel, is guided at the driver section in the cam track and is operatively connected at the connection section to the actuation rod, which extends perpendicular, i.e. at right angles, to the axis of rotation of the cam wheel. Furthermore, the actuation device has a bearing device which provides positive guidance of the cam-follower pin along the longitudinal axis. Here, "positive guidance" means a mechanical guidance of the cam-follower pin by the bearing device, by which the possibility of movement of the cam-follower pin is reduced to one degree of freedom, namely the forward and backward movement along the longitudinal axis. Thus, rotation of the cam wheel about its axis of rotation results in a linear movement of the cam-follower pin guided in the cam track and therefore of the operatively connected actuation rod along the longitudinal axis. Thus, a linear movement of the actuation rod operatively connected to the cam-follower pin is achieved by the corresponding arrangement of the cam wheel with respect to the actuation rod. In this way, the rotational movement of a drive motor is converted into a linear movement of the actuation rod, such that, by advancement and retraction of the actuation rod, the jaw parts can be actuated for opening and closing.

In order to achieve a high closing force of the jaw part mechanism, the transmission ratio between the drive motor and the jaw parts can be selected as high as possible according to the disclosure. In a preferred embodiment of the actuation device according to the disclosure, it is provided that the cam wheel has, at least along a predetermined circumferential portion, a drive ring which is operatively connected to a drive element that can be actuated by a motor via a drive shaft. The design of the drive ring with respect to the drive element can be chosen such that the force and speed for moving the actuation rod are transmitted in a manner adapted to the particular use of the instrument.

In a preferred embodiment of the actuation device according to the disclosure, the drive ring can be a gear ring, and the drive element engaging therewith is a pinion, such that the transmission ratio can be set to the desired level through the ratio of the diameter or teeth of pinion and gear ring. The gear ring can be a spur gear ring, a bevel gear ring or a worm gear ring, the pinion being provided as a corresponding spur gear, bevel gear or worm shaft.

However, the term "drive ring" is not to be understood here as limited to a gear ring, and instead it comprises drive variants that act in the same way, for example a tension mechanism pulley, which is operatively connected by a tension means to the drive element likewise designed as a tension mechanism pulley, wherein the transmission ratio can be adjusted by the choice of the diameters of the tension mechanism pulley.

In another embodiment of the actuation device according to the disclosure, it is provided that the cam track extends over a portion along an Archimedean spiral about the axis of rotation, wherein opposite directions of rotation of the cam wheel lead to opposite linear movements of the cam-follower pin along the longitudinal axis and thus to the forward and backward movement of the actuation rod.

Since in the Archimedean spiral the radius increases proportionally to the angle of rotation during a rotational movement, i.e. the gradient (increase in radius depending on the angle of rotation) is constant, the cam-follower pin guided in the cam track thus formed is moved uniformly linearly. The extent and speed of the linear movement therefore depends on the length and gradient of the cam. If the cam wheel is moved in a first direction of rotation, the cam-follower pin guided in the cam track is moved linearly in a first direction along the longitudinal axis, as a result of which the actuation rod is advanced, for example in order to open the jaw parts of the surgical instrument. In this example, the closing of the jaw parts is accordingly effected by retraction of the actuation rod, by means of the cam-follower pin being moved linearly along the longitudinal axis in a second direction of rotation counter to the first direction of rotation, which in this embodiment is achieved by changing the direction of rotation of the cam wheel to a second direction of rotation counter to the first direction of rotation. Of course, an actuation mechanism can also be provided in which, conversely, the jaw parts are opened by the retraction of the actuation rod and the jaw parts are closed by the advancing of the actuation rod. In this embodiment, it is possible that a drive ring does not have to be formed completely circumferentially if the range of movement of the cam-follower pin guided in the cam track does not require a full rotation of the cam wheel.

As an alternative to the shape of the cam track corresponding to a section along an Archimedean spiral about the axis of rotation, the cam track can be based on a section of a spiral with a variable gradient, i.e. can have variable increases in radius depending on the angle of rotation, in which case the opposite linear movements of the cam-follower pin along the longitudinal axis are effected by opposite directions of rotation of the cam wheel about the axis of rotation. Non-limiting examples include logarithmic, hyperbolic or Fermat spirals, but also clothoids or combinations of all of the above, including Archimedean spirals. Here, combinations mean that the cam track can be divided into two or more sections, which can be based on different spiral types with different gradient functions. On account of the variable gradient of the cam track, it is possible to individually control the speed and the force-to-travel ratio of the linear movement. The gradient of the cam track can be used to influence the adjustment speed and also the distribution force or transmission ratio: A shallow gradient of the cam track (at a constant rotational speed of the cam wheel) leads to slow linear movement with higher force. A higher gradient of the cam track results in more rapid linear movement and lower force. If a spiral with a non-constant gradient is used, the actuation device can for example be adjusted such that, with a constant rotational movement, a rapid linear movement can be generated at the start by a large spiral gradient and, in the end region, a slow linear movement, but at the same time a high closing force, can be generated by a shallow spiral gradient. However, other versions of the cam track gradient are also conceivable, even a reversal of direction.

As an alternative to the aforementioned embodiment, the cam track can be constructed in a manner that provides a back and forth movement of the cam-follower pin along the longitudinal axis, for advancing and retracting the actuation rod, without changing the direction of rotation of the cam wheel. For this purpose, in a further embodiment of the actuation device according to the disclosure, the cam track extends over at least two sections that have different gradients and form a closed cam track. In this case, the first section is designed for the linear movement of the cam-follower pin in a first direction along the longitudinal axis as the cam wheel rotates about the rotation axis in a predetermined direction of rotation. The second section is designed for the linear movement of the cam-follower pin in a second direction, counter to the first direction, along the longitudinal axis as the cam wheel rotates further about the rotation axis in the predetermined direction of rotation. Here again, at least one of the sections can extend along an Archimedean spiral and/or the speed and the force-to-travel ratio of the linear movement can be individually controlled by a variable gradient of the cam track. For example, for the closing movement of the jaw parts by movement of the actuation rod, a speed and a force-to-travel ratio can be selected different than that for the opening movement.

To ensure that the cam-follower pin is guided free of friction in the cam track and does not execute a rotational movement, it is provided, in a further embodiment of the actuation device according to the disclosure, that the cam-follower pin is mounted and guided in the cam track. For this purpose, one or more (radial) bearings, e.g. rolling bearings, can be arranged on the driver section of the cam-follower pin, via which bearings the cam-follower pin is mounted in the cam track. Preferably, the driver section can be limited on both sides by shaft steps, in order in each case to provide a stop for two bearings. Alternatively, the cam-follower pin can mounted and guided slidably in the cam track by means of a suitable material pairing.

In principle, it is conceivable that, in one embodiment of the actuation device according to the disclosure, the cam-follower pin for transmitting the linear movement is directly connected to the actuation rod, for example by screwing or welding, or also by manufacturing the cam-follower pin and actuation rod in one piece, wherein the bearing device of the actuation device provides for the positive guidance along the longitudinal axis. In another embodiment of the actuation device according to the disclosure, the operative connection of the cam-follower pin to the actuation rod is provided by the bearing device, which has a longitudinal bore through which the actuation rod extends and has a driver bore perpendicular to the longitudinal bore, in which the connection portion of the cam-follower pin is received.

The bearing device is arranged axially movably along the longitudinal axis in a guide block, which for this purpose has a bearing opening along the longitudinal axis. Preferably, the guide block in the bearing opening can provide a plain bearing of the bearing device. For the longitudinal axial mobility, the bearing device and the bearing opening in the guide block are formed corresponding to each other in a cylindrical or prismatic shape with a lateral surface parallel to the longitudinal axis, wherein the guide block has, for the cam-follower pin, a through-opening or guide groove communicating with the bearing opening and extending parallel to the longitudinal axis. In this way, the bearing device is fixed with respect to all degrees of freedom except the longitudinal forward and backward movement. Furthermore, in contrast to the circular shape, corresponding cross-sectional shapes of the bearing device and bearing opening that prevent a rotation of the bearing device about the longitudinal axis permit alternative designs in which the cam-follower pin, guided in the through-opening or guide groove of the guide block to prevent rotation about the longitudinal axis, is not fixed in a radial driver bore.

If the bearing fixture is firmly connected to the actuation rod, then the actuation rod, as in the case of the direct connection of the cam-follower pin and the actuation rod, can provide only the linear movement for opening and closing the jaw parts. Therefore, in a preferred embodiment of the actuation device according to the disclosure, which advantageously also permits a rotational movement of the actuation rod as an additional actuation mechanism, it is provided that the bearing device, which has the longitudinal bore and perpendicular thereto the driver bore, is composed of at least two housing parts which, at front ends facing each other, are connected to each other in a plane perpendicular to the longitudinal axis. In this case, receiving openings are formed in the mutually facing end faces coaxially to the longitudinal bore, which receiving openings each provide a bearing seat for a clamping disk bearing arrangement, the latter providing a rotatable mounting of the actuation rod in the bearing device with axial fixation for transmitting the linear movement from the cam-follower pin to the actuation rod. For this purpose, in a preferred embodiment, the clamping disk bearing arrangement can have a clamping plate, which is connected to the actuation rod and therefore rotatable about the longitudinal axis. Furthermore, the clamping disk bearing arrangement comprises two axial bearings in order to rotationally decouple the intermediate clamping disk from the bearing device, wherein the axial bearings are arranged on the bearing seats in the receiving openings of the housing parts. The clamping plate is thus fixed axially in the bearing device and can preferably be arranged between two flanges, which each provide a bearing seat for the bearing ring of the axial bearings that faces the clamping plate.

A surgical instrument according to the disclosure, which has a hollow shaft with, at the distal end, a tool having at least two jaw parts and, at the proximal end, an actuation device which is operatively connected to an actuation rod, which is mounted axially movably in the shaft in the direction of a longitudinal axis of the shaft in order to open and close the jaw parts, has an actuation device in one embodiment according to the disclosure.

Further embodiments, and some of the advantages associated with these and with further embodiments, are made clear and more understandable by the following detailed description which makes reference to the attached figures. Objects or parts thereof which are substantially the same or similar may be provided with the same reference signs. The figures are merely a schematic illustration of an embodiment of the disclosure. The drawings, the description and the claims contain numerous features in combination. A person skilled in the art will advantageously also consider the features on an individual basis and combine them to form further advantageous combinations.

6

Figures 2, 3:
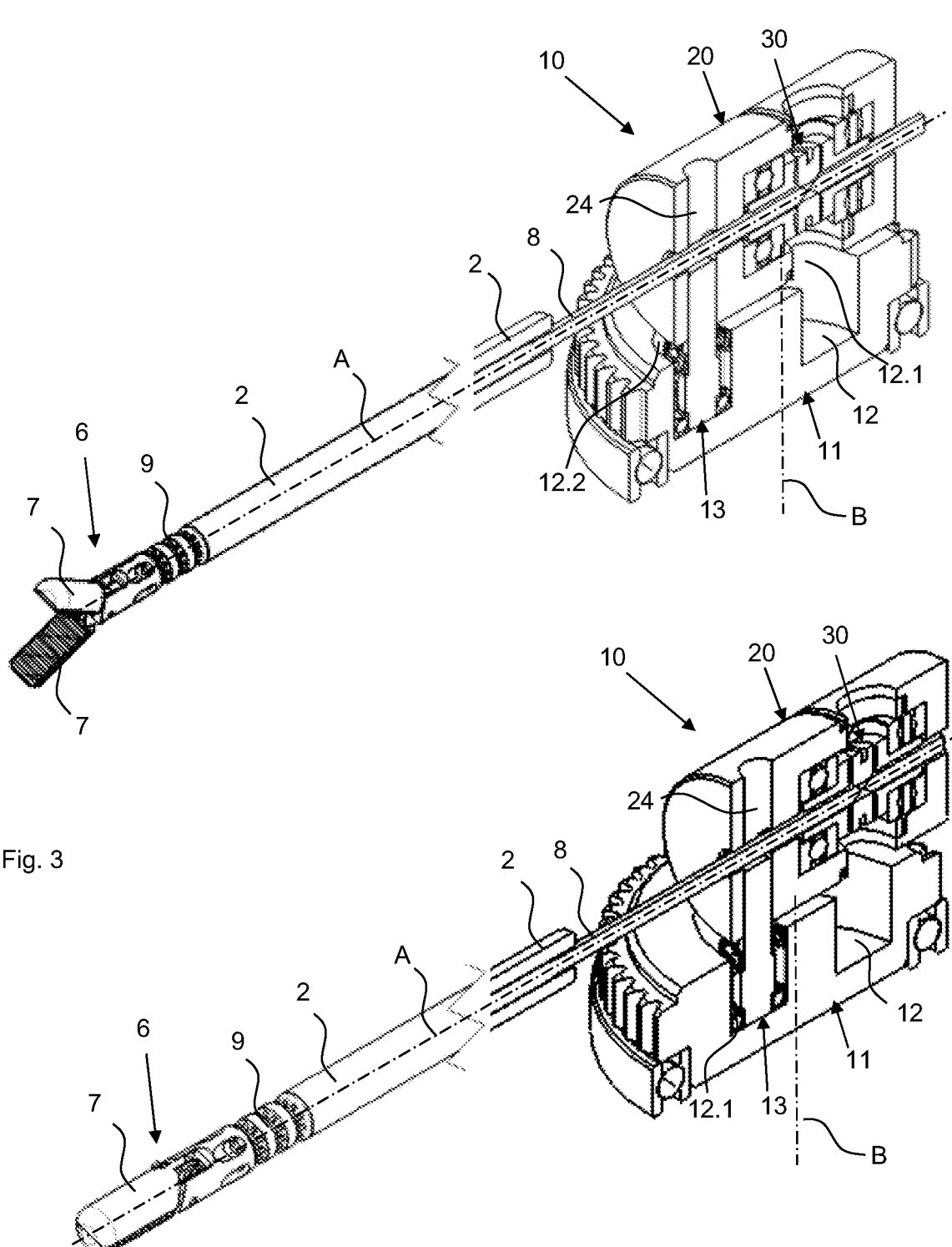
FIG. 2 shows a perspective view of the tool tip with opened jaw parts, and a perspective sectional view of an actuation device according to the invention.
FIG. 3 shows a representation according to FIG. 2 with closed jaw parts.
Figure 5:
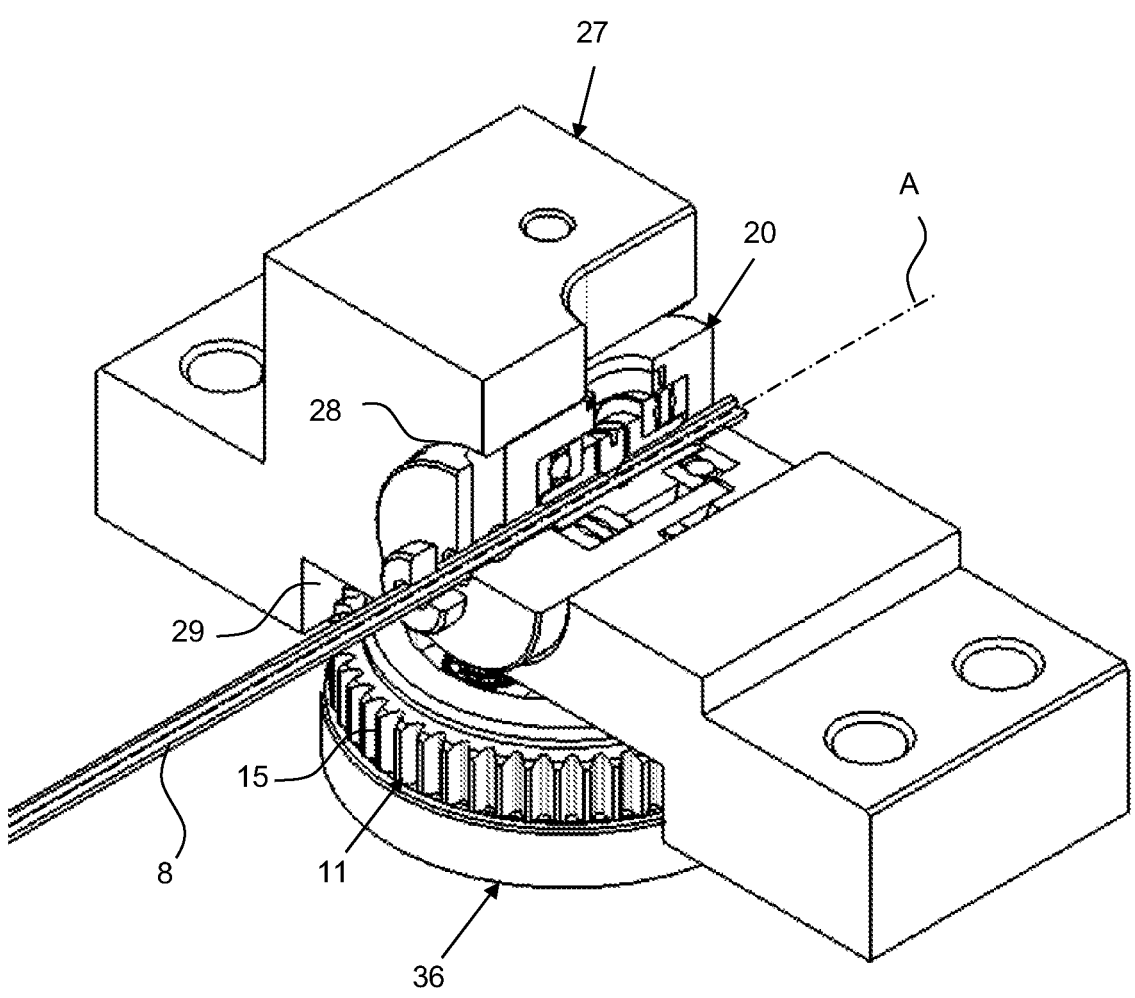
Figure 6:
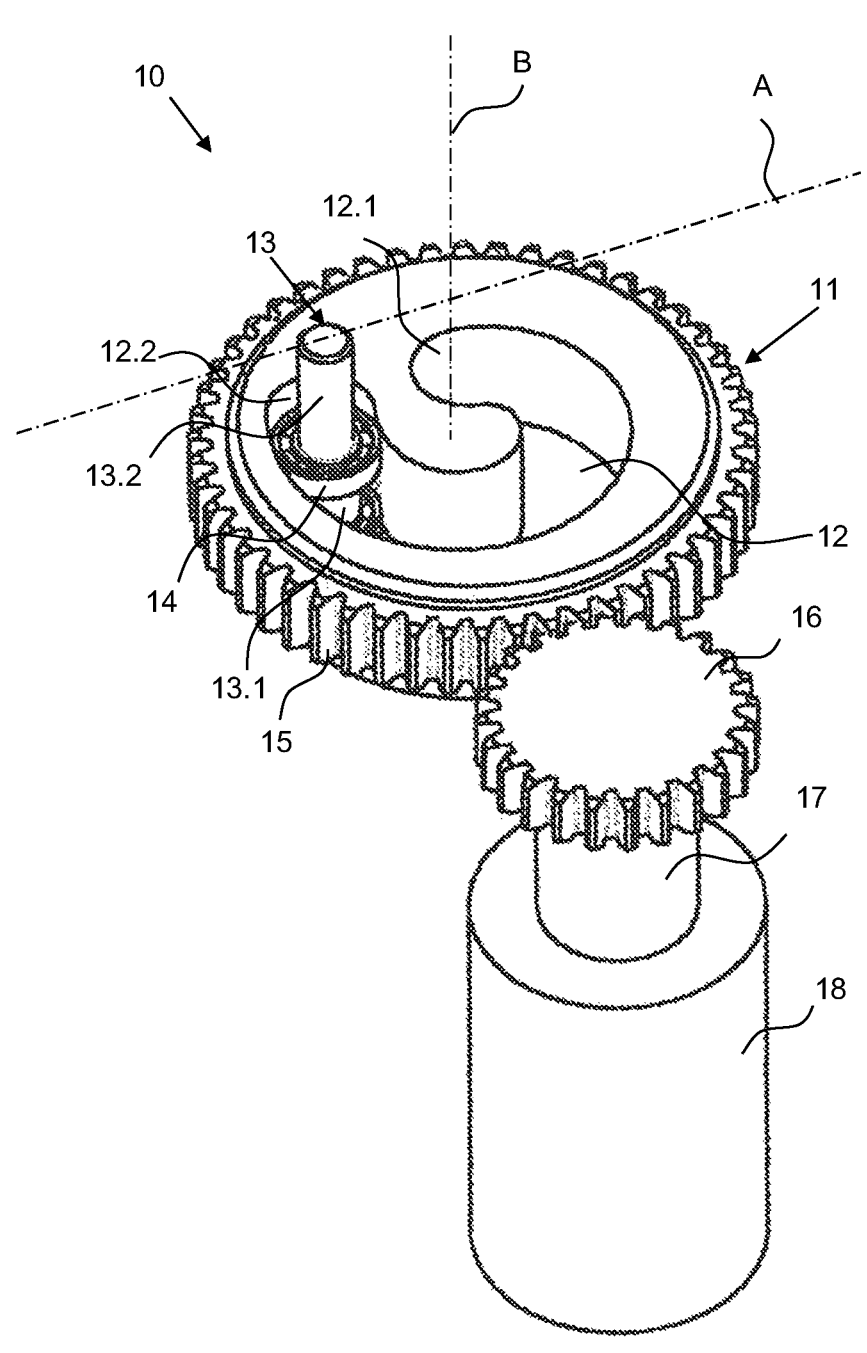

FIG. 5 shows a partial perspective sectional view of the actuation device according to the invention from FIG. 2 with a guide block, FIG. 6 shows a detailed perspective view of an actuation device according to the disclosure.

DETAILED DESCRIPTION OF PREFERRED EMBODIMENTS

Figure 1:
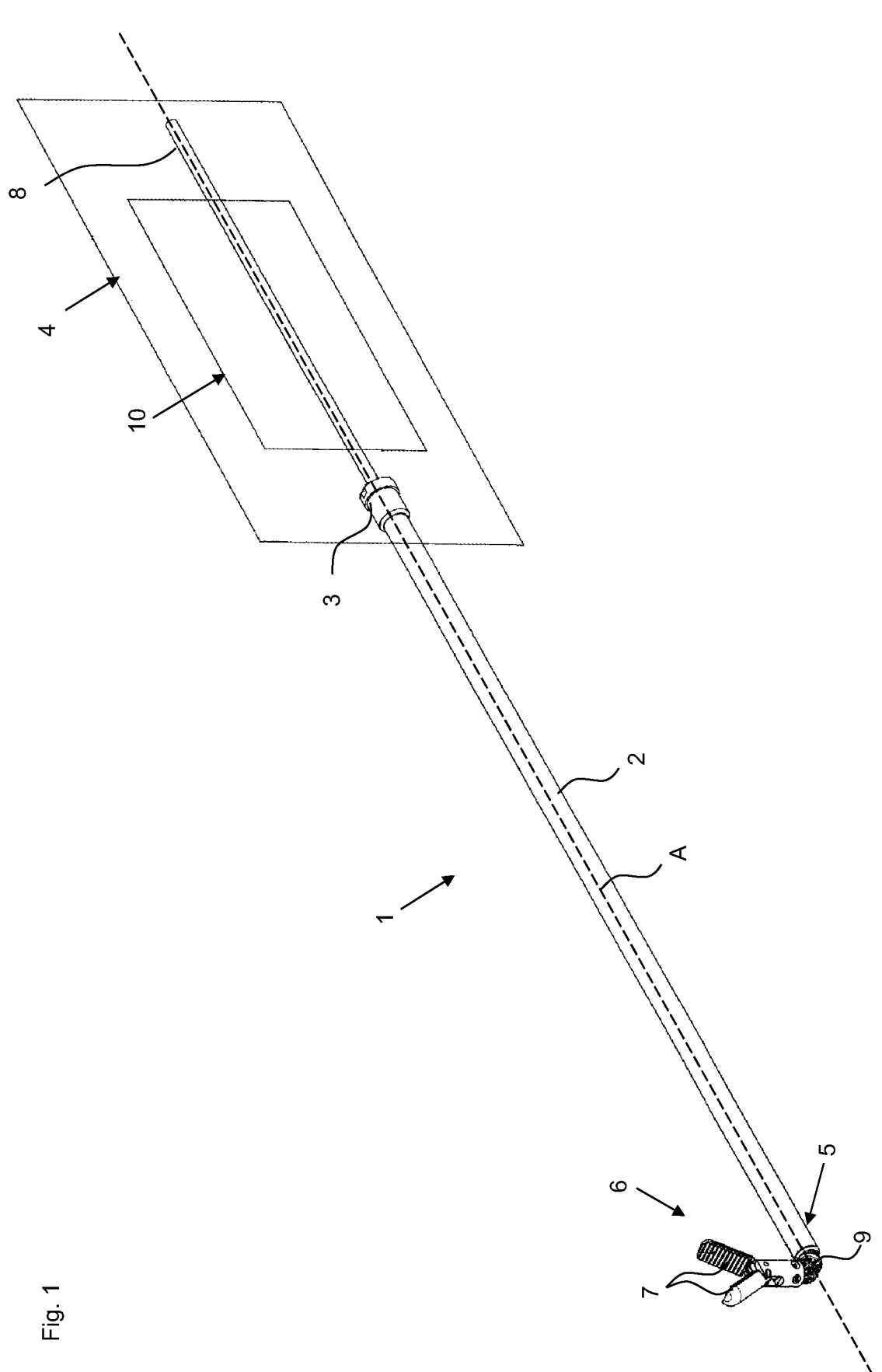
FIG. 1 shows a schematic perspective side view of a surgical instrument.

FIG. 1 shows schematically a surgical instrument 1 comprising a hollow shaft 2, a handle or actuation unit 4 (indicated only schematically) arranged at the proximal end 3 of the shaft 2, and a tool 6 arranged at the distal end 5 of the shaft 2 and having two jaw parts 7, which are designed here as a gripping tool.

As an alternative to the tool 6 shown in FIGS. 1 to 3, in which the two jaw parts 7 form a gripping tool, the jaw parts of the tool of a surgical instrument according to the disclosure may also be designed for cutting, for example. Furthermore, it is conceivable that a tool for gripping can also have more than two jaw parts, for example three or more jaw parts, which can be opened by spacing them apart from each other and closed by bringing them close to each other.

The tool 6, which can also be pivoted via a joint mechanism 9 relative to the longitudinal axis A of the shaft 2 with an actuation mechanism (not described herein), can be actuated via an actuation rod 8 mounted axially displaceably in the shaft 2 in the direction of the longitudinal axis A, the proximal end of which actuation rod 8 is operatively connected to the actuation unit 4 via an actuation device 10.

The actuation unit 4 can preferably be designed for robotic use and can thus also be a structural unit operable without manual intervention-which is advantageous for the reproducibility of the actuation. The actuation rod 8 mounted axially displaceably in the shaft 2, and serving to actuate the tool 6 consisting of two jaw parts 7, is designed as a pull/push rod.

In FIG. 2, the jaw parts 7 of the tool 6 at the distal end of the shaft 2 are opened by retracting the actuation rod 8 by means of an actuation device 10 according to the disclosure, and in FIG. 3 the jaw parts 7 of the tool 6 at the distal end of the shaft 2 are in the closed state after the actuation rod 8 has been advanced by means of the actuation device 10 according to the disclosure. Here, "retraction" means a movement of the actuation rod 8 in the proximal direction (toward the right in the figure) and "advance" consequently means a movement of the actuation rod 8 in the distal direction (toward the left in the figure).

The basic concept of an actuation device 10 according to the disclosure is illustrated in an exemplary embodiment in FIG. 6. The actuation device 10 has a cam wheel 11 with a cam track 12 which extends along a portion of an Archimedean spiral about the axis of rotation B of the cam wheel 11, which axis extends perpendicular to the longitudinal axis A of the surgical instrument. A cam-follower pin 13 is guided in the cam track 12, which cam-follower pin 13 extends parallel to the axis of rotation B of the cam wheel 11 and is mounted on a driver section 13.1 in the cam track 12 via the bearing 14 in the cam track 12. The length and slope of the cam track 12 depend on the displacement path provided for the actuation rod 8 and on the desired displacement speed and can accordingly be calculated without further ado.

A connection section 13.2 of the cam-follower pin 13 is operatively connected to the actuation rod 8 (not shown in FIG. 6, but in FIGS. 2 to 5, which comprise the detail from FIG. 6 in section), which extends along the longitudinal axis A. By being defined in relation to the longitudinal axis A by means of the bearing device 20, the cam-follower pin 13 follows the curve track 12 during rotation of the cam wheel 11 about the axis of rotation B and executes a linear movement along the longitudinal axis A. The rotation of the cam wheel 11 is generated by a drive element, here a spur gear 16, which is driven by a motor 18 via a drive shaft 17 and which is in engagement with a spur gear ring 15 formed on the circumference of the cam wheel 11. A high transmission ratio between gear ring 15 and pinion 16 ensures a high torque for moving the actuation rod and thus a high clamping force of the jaw part mechanism.

Further drive configurations (not shown) for transmitting the adjustment movements of the motor 18 to the cam wheel 11 comprise, for example, a bevel gear ring or a worm gear ring as drive ring, wherein the drive element is correspondingly a bevel gear or a worm shaft. Alternatively, the drive ring and the drive element can also be formed by tension mechanism pulleys, for example belt pulleys or toothed pulleys, which are operatively connected by a pulling means such as a toothed belt or a chain.

In the case of the cam wheel 11 shown in FIGS. 2 to 6, the Archimedean spiral, which the cam track 12 follows along a notch, runs to the right when viewed from above, i.e. the radius of the spiral increases clockwise, so that a first end 12.1 (FIG. 6) of the cam track 12 is closer to the axis of rotation B and the second end 12.2 is closer to the circumference of the cam track 12. Of course, in an alternative embodiment not shown here, a cam track of an actuation device according to the disclosure can also run to the left, so that the radius of the spiral increases counterclockwise.

Figure 4:
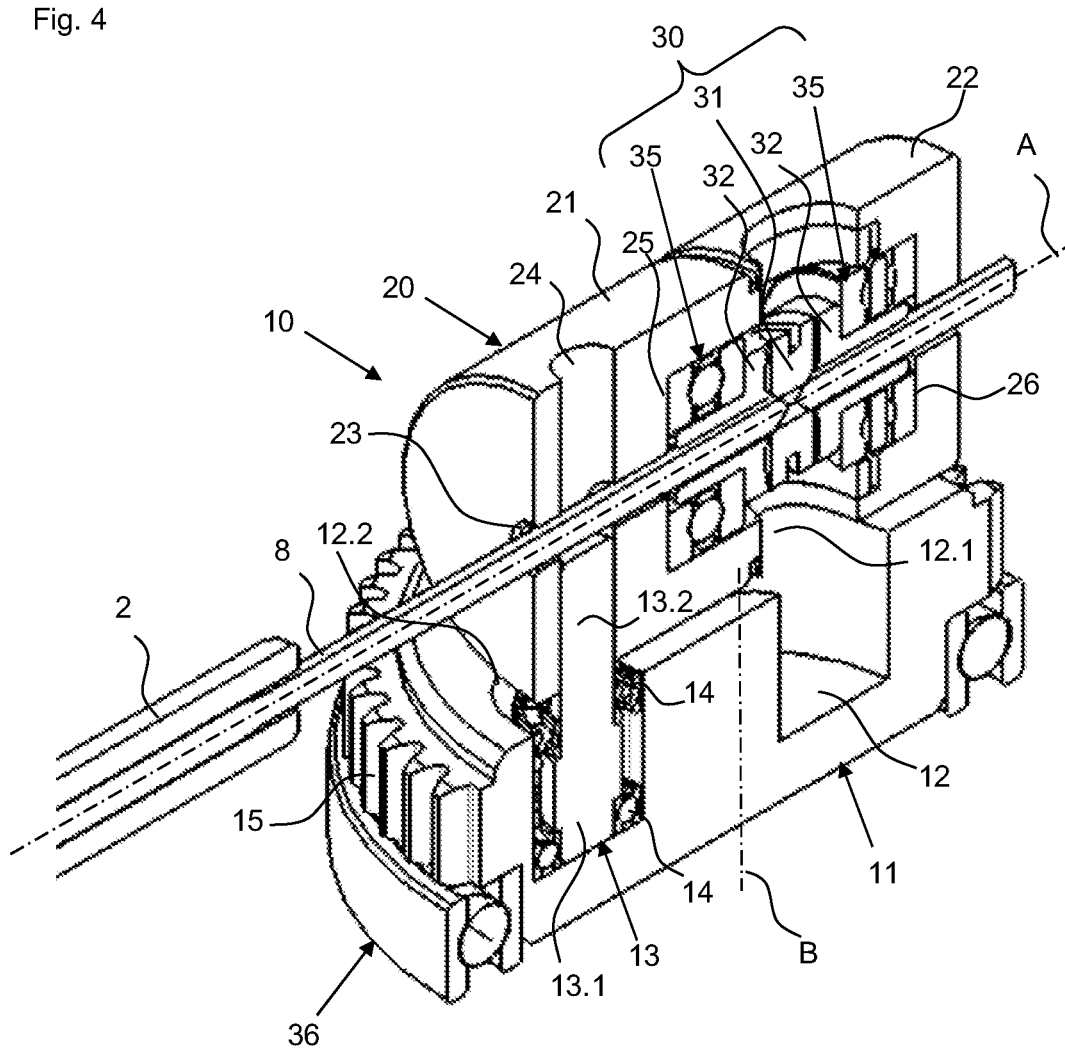
FIG. 4 shows an enlarged perspective sectional view of the actuation device according to the invention from FIG. 2.

The cam track 12 shown is designed to move the cam-follower pin 13 linearly in a first direction along the longitudinal axis A upon rotation of the cam wheel 11 in a first direction of rotation, and, when the cam wheel 11 mounted rotatably in a bearing 36 rotates in a second direction of rotation counter to the first direction of rotation, the cam-follower pin 13 is moved linearly along the longitudinal axis A in a second direction counter to the first direction. In the example shown, the actuation rod 8, operatively connected to the cam-follower pin 13, is retracted in order to open the jaw parts 7 of the tool 6 (FIG. 2) when the scanning pin 13, as also shown in FIGS. 4 and 6, is present at the second end 12.2 of the cam track 12, i.e. the end near the circumference. If the cam wheel 11 is now driven clockwise about the axis of rotation B, the actuation pin 13 follows the cam track 12 in the direction of the first end 12.1, the end near the axis, and executes a linear movement along the longitudinal axis A (towards the left in the figures), such that the actuation rod 8 (cf. FIG. 3) operatively connected thereto is advanced and, in this way, the jaw parts 7 of the tool 6 at the tip of the instrument are closed. Of course, in a modification (not shown) of a surgical instrument according to the disclosure, conversely the jaw parts can be closed by retraction of the actuation rod and the jaw parts can be opened by advance of the actuation rod.

In a departure from the cam track 12 shown in FIGS. 2 to 4, which corresponds to a section of an Archimedean spiral about the axis of rotation B, a cam track of an actuation device according to an alternative embodiment (not shown) could be constructed with a variable gradient, in order to individually control the speed and force-to-travel ratio of the linear movement.

Furthermore, a variant with a closed cam track is conceivable, which allows the linear movement of the cam-follower pin in both directions along the longitudinal axis A and thus the advance and retraction of the actuation rod without changing the direction of rotation of the cam wheel.

As can be seen particularly clearly in the detailed representation of the actuation device 10 in FIG. 4, the cam-follower pin 13 in the example shown has a driver section 13.1, which is limited on both sides by shaft steps which are formed by a corresponding change in the diameter of the cylindrical cam-follower pin 13, such that the driver section 13.1 has a greater diameter between the shaft steps. In this way, the shaft steps on the driver section 13.1 of the cam-follower pin 13 each form a stop for a respective radial bearing 14, via which the cam-follower pin 13 is mounted in the cam track 12, such that the cam-follower pin 13, on passing through the cam track 12, does not execute a rotational movement upon rotation of the cam wheel 11. Alternatively, bearing variants with a single roller bearing or more than two roller bearings or a version as a plain bearing are also conceivable.

In the example shown in FIGS. 2 to 4 and 6, the operative connection of the cam-follower pin 13 to the actuation rod 8 is provided by the connection section 13.2 which adjoins the driver section 13.1 and via which the cam-follower pin is connected to a bearing device 20, the latter having a central longitudinal bore 23 for the actuation rod 8 and, perpendicular to it, a driver bore 24 in which the connection section 13.2 of the cam-follower pin 13 is received preferably free of play. In the example shown, the driver bore 24 extends completely through the diameter of a first housing part 21 of the bearing device 20 and crosses the longitudinal bore 23 through which the actuation rod 8 extends. The connection section 13.2 of the actuation pin 13 is dimensioned such that it extends to the longitudinal bore 23 at most and does not contact the actuation rod 8, since the latter is arranged rotatably about the longitudinal axis A in the longitudinal bore 23 in the bearing device 20.

In an alternative not shown, it is therefore also possible that the driver bore, in a departure from the illustrated example, extends only partially through the bearing device 20 and ends, for example, at or in front of the longitudinal bore.

FIG. 5 illustrates an example of a positive guidance of the cam-follower pin 13 along the longitudinal axis A, as provided by the bearing device 20. For this purpose, the bearing device 20, which is formed here with a circular cross-section, is mounted slidably along the longitudinal axis A in a bearing opening 28 of a guide block 27 with a corresponding circular cross-section. In the example shown, the guide block 27 also has a recess 29 for receiving the cam wheel 11. In the guide block 27, there is a through-opening or guide groove (not visible in the figure), which is formed parallel to the longitudinal axis A, in the example shown between the bearing opening 28 and the recess 29. This through-opening or guide groove has a length which corresponds at least to a distance traveled by the cam-follower pin 13, which extends through this through-opening or guide groove to the bearing device 20 received in the bearing opening 28, in the cam track 12 upon rotation of the cam wheel 11. In this way, the bearing device 20 is fixed with respect to all degrees of freedom except the longitudinal axial forward and backward movement. As an alternative to the example shown, a bearing device and the corresponding bearing opening in the guide block can have a cross-section deviating from the circular shape, for example an elliptical or polygonal cross-section, such that the rotation of the bearing device is already prevented by its shape.

For the rotatable arrangement of the actuation rod 8 in the longitudinal bore 23 of the bearing device 20, the latter houses a clamping disk bearing arrangement 30 in order to transmit the linear movement of the cam-follower pin 13 to the actuation rod 8 without preventing its rotation. For this purpose, the bearing device 20 in the example shown has two housing parts 21, 22 which, at front ends facing each other, are connected to each other in a plane perpendicular to the longitudinal axis A. Of course, a bearing device of an actuation device according to the disclosure can also have more than two housing parts and/or can have separating or connecting planes that deviate from the example shown.

In the mutually facing front ends of the housing parts 21, 22, receiving openings are formed coaxially to the longitudinal bore 23 in order to receive the clamping disk bearing arrangement 30. The first, distal-side housing part 21, which here has the driver bore 24, provides, together with the receiving opening coaxial to the longitudinal bore 23, a bearing seat 25 for a first axial bearing 25 (designed as a ball bearing in FIGS. 2-4). Similarly, the receiving opening of the second, proximal-side housing part 22 forms a bearing seat 26 for a second axial bearing 35 (here designed as a needle bearing). A clamping disk 31, connected to the actuation rod 8, is mounted between the axial bearings 35, in each case via a flange 32. The flanges 32 provide the bearing seats for the bearing shells of the axial bearings 35 facing the clamping disk 31, through which the clamping disk 31 fixed axially by means of the flanges 32 can rotate with the actuation rod 8 about the longitudinal axis A in the bearing device 20.

Equivalent alternatives to the clamping disk and to the clamping disk bearing arrangement are readily conceivable and are therefore merely obvious modifications of the actuation device according to the disclosure within the scope of protection.

The drawings, the description and the claims contain numerous features in combination. A person skilled in the art will advantageously also consider the features on an individual basis and combine them to form further advantageous combinations. The present disclosure relates to an actuation device 10 for a surgical instrument 1 and to a corresponding surgical instrument 1 comprising a hollow shaft 2 with a tool 6 at the distal end 5 of the shaft 2, wherein the tool 6 has at least two jaw parts 7, and the actuation device 10 is arranged at the proximal end 3 of the shaft 2 and is operatively connected to an actuation rod 8 which is mounted in the shaft 2 so as to be movable axially in the direction of a longitudinal axis A of the shaft 2 in order to open and close the jaw parts 7. The actuation device 10 has a cam wheel 11 with a cam track 12 and a cam-follower pin 13 which is guided on a driver section 13.1 in the cam track 12 and is operatively connected to the actuation rod 8 at a connection section 13.2, wherein the actuation device 10 has a bearing device 20, which provides positive guidance of the cam-follower pin 13 along the longitudinal axis A, such that, during rotation of the cam wheel 11 about an axis of rotation B of the cam wheel 11 perpendicular to the longitudinal axis A, a linear movement of the cam-follower pin 13, guided in the cam track 12, and of the actuation rod 8 operatively connected thereto is provided along the longitudinal axis A.

The invention claimed is:

1. An actuation device for a surgical instrument including a hollow shaft with a tool at the distal end of the shaft, wherein the tool has at least two jaw parts, and the actuation device is arranged at the proximal end of the shaft and is operatively connected to an actuation rod which is mounted in the shaft so as to be movable axially in the direction of a longitudinal axis of the shaft in order to open and close the jaw parts, the actuation device comprising:

a cam wheel with a cam track and a cam-follower pin which is guided on a driver section in the cam track and is operatively connected to the actuation rod at a connection section, the cam wheel has, at least along a predetermined circumferential portion, a drive ring which is operatively connected to a drive element, which can be actuated by a motor, wherein the drive ring is a gear ring, and the drive element engaged therewith is a pinion, or the drive ring and the drive element are formed by means of pulleys which are operatively connected by a tension means; and a bearing device, which provides positive guidance of the cam-follower pin along the longitudinal axis, such that, during rotation of the cam wheel about an axis of rotation of the cam wheel perpendicular to the longitudinal axis, a linear movement of the cam-follower pin, guided in the cam track, and of the actuation rod operatively connected thereto is provided along the longitudinal axis.

2. The actuation device as set forth in claim 1, wherein the cam track extends over a section along an Archimedean spiral about the axis of rotation or has a variable gradient, wherein opposite directions of rotation of the cam wheel about the axis of rotation provide opposite linear movements of the cam-follower pin along the longitudinal axis.

3. The actuation device as set forth in claim 1, wherein the cam track extends over at least two sections forming a closed cam track, wherein a first section is designed for the linear movement of the cam-follower pin in a first direction along the longitudinal axis upon rotation of the cam wheel about the axis of rotation in a predetermined direction of rotation, and a second section is designed for the linear movement of the cam-follower pin in a second direction, counter to the first direction, along the longitudinal axis as the cam wheel rotates about the axis of rotation in the predetermined direction of rotation.

4. The actuation device as set forth in claim 1, wherein the cam-follower pin is guided and mounted in the cam track, wherein at least two bearings are arranged on the driver section of the cam-follower pin, via which bearings the cam-follower pin is mounted in the cam track, wherein the driver section is limited on both sides by shaft steps, which each provide a stop for the two bearings.

5. The actuation device as set forth in claim 1, wherein the bearing device, which has a longitudinal bore through which the actuation rod extends and has a driver bore, perpendicular to the longitudinal bore, in which the connection section of the cam-follower pin is received, is arranged axially movably along the longitudinal axis in a guide block which has a bearing opening along the longitudinal axis, wherein the guide block provides a plain bearing of the bearing device in the bearing opening.

6. The actuation device as set forth in claim 5, wherein the bearing device has at least two housing parts which, at front ends facing each other, are connected to each other in a plane perpendicular to the longitudinal axis, wherein receiving openings are formed in the mutually facing end faces coaxially to the longitudinal bore, which receiving openings each provide a bearing seat for a clamping disk bearing arrangement, the latter having a clamping plate, which is connected to the actuation rod, and two axial bearings, which are arranged in the bearing seats, which is arranged between two flanges, is mounted between the axial bearings.

7. An actuation device for a surgical instrument including a hollow shaft with a tool at the distal end of the shaft, wherein the tool has at least two jaw parts, and the actuation device is arranged at the proximal end of the shaft and is operatively connected to an actuation rod which is mounted in the shaft so as to be movable axially in the direction of a longitudinal axis of the shaft in order to open and close the jaw parts, the actuation device comprising:

a cam wheel with a cam track and a cam-follower pin which is guided on a driver section in the cam track and is operatively connected to the actuation rod at a connection section; and a bearing device, which provides positive guidance of the cam-follower pin along the longitudinal axis, such that, during rotation of the cam wheel about an axis of rotation of the cam wheel perpendicular to the longitudinal axis, a linear movement of the cam-follower pin, guided in the cam track, and of the actuation rod operatively connected thereto is provided along the longitudinal axis; and wherein the cam track extends over a section along an Archimedean spiral about the axis of rotation or has a variable gradient, wherein opposite directions of rotation of the cam wheel about the axis of rotation provide opposite linear movements of the cam-follower pin along the longitudinal axis.

8. An actuation device for a surgical instrument including a hollow shaft with a tool at the distal end of the shaft, wherein the tool has at least two jaw parts, and the actuation device is arranged at the proximal end of the shaft and is operatively connected to an actuation rod which is mounted in the shaft so as to be movable axially in the direction of a longitudinal axis of the shaft in order to open and close the jaw parts, the actuation device comprising:

a cam wheel with a cam track and a cam-follower pin which is guided on a driver section in the cam track and is operatively connected to the actuation rod at a connection section; and a bearing device, which provides positive guidance of the cam-follower pin along the longitudinal axis, such that, during rotation of the cam wheel about an axis of rotation of the cam wheel perpendicular to the longitudinal axis, a linear movement of the cam-follower pin, guided in the cam track, and of the actuation rod operatively connected thereto is provided along the longitudinal axis; and wherein the cam track extends over at least two sections forming a closed cam track, wherein a first section is designed for the linear movement of the cam-follower pin in a first direction along the longitudinal axis upon rotation of the cam wheel about the axis of rotation in a predetermined direction of rotation, and a second section is designed for the linear movement of the cam-follower pin in a second direction, counter to the first direction, along the longitudinal axis as the cam wheel rotates about the axis of rotation in the predetermined direction of rotation.

9. An actuation device for a surgical instrument including a hollow shaft with a tool at the distal end of the shaft, wherein the tool has at least two jaw parts, and the actuation device is arranged at the proximal end of the shaft and is operatively connected to an actuation rod which is mounted in the shaft so as to be movable axially in the direction of a longitudinal axis of the shaft in order to open and close the jaw parts, the actuation device comprising:

a cam wheel with a cam track and a cam-follower pin which is guided on a driver section in the cam track and is operatively connected to the actuation rod at a connection section; and a bearing device, which provides positive guidance of the cam-follower pin along the longitudinal axis, such that, during rotation of the cam wheel about an axis of rotation of the cam wheel perpendicular to the longitudinal axis, a linear movement of the cam-follower pin, guided in the cam track, and of the actuation rod operatively connected thereto is provided along the longitudinal axis; and wherein the bearing device, which has a longitudinal bore through which the actuation rod extends and has a driver bore, perpendicular to the longitudinal bore, in which the connection section of the cam-follower pin is received, is arranged axially movably along the longitudinal axis in a guide block which has a bearing opening along the longitudinal axis, wherein the guide block provides a plain bearing of the bearing device in the bearing opening.

10. The actuation device as set forth in claim 9, wherein the bearing device has at least two housing parts which, at front ends facing each other, are connected to each other in a plane perpendicular to the longitudinal axis, wherein receiving openings are formed in the mutually facing end faces coaxially to the longitudinal bore, which receiving openings each provide a bearing seat for a clamping disk bearing arrangement, the latter having a clamping plate, which is connected to the actuation rod, and two axial bearings, which are arranged in the bearing seats, which is arranged between two flanges, is mounted between the axial bearings.

* * * * *